US00PP22046P2

(12) United States Plant Patent
Giesen

(10) Patent No.: US PP22,046 P2
(45) Date of Patent: Jul. 26, 2011

(54) ***SOLENOSTEMON* PLANT NAMED 'MOS AMAGREN'**

(50) Latin Name: *Solenostemon scutellarioides*
Varietal Denomination: Mos Amagren

(75) Inventor: Eric Giesen, Andijk (NL)

(73) Assignee: Syngenta Crop Protection AG, Basel (CH)

( * ) Notice: Subject to any disclaimer, the term of this patent is extended or adjusted under 35 U.S.C. 154(b) by 0 days.

(21) Appl. No.: 12/804,343

(22) Filed: Jul. 20, 2010

(51) Int. Cl.
*A01H 5/00* (2006.01)

(52) U.S. Cl. ..... Plt./373

(58) Field of Classification Search ..... Plt./373
See application file for complete search history.

*Primary Examiner* — Kent L Bell
(74) *Attorney, Agent, or Firm* — S. Matthew Edwards

(57) ABSTRACT

A new *Solenostemon* plant named 'Mos Amagren' particularly distinguished by the light yellow, yellow-green and red-purple colored foliage with an upright, well branched and uniform plant habit.

1 Drawing Sheet

Latin name of the genus and species of the plant claimed: *Solenostemon scutellarioides*.

Varietal denomination: 'Mos Amagren'.

BACKGROUND OF THE NEW PLANT

The present invention comprises a new *Solenostemon*, botanically known as *Solenostemon scutellarioides*, and hereinafter referred to by the variety name 'Mos Amagren'.

'Mos Amagren' is a product of a planned breeding program. The new cultivar has light yellow, yellow-green and red-purple colored foliage, with an upright, well branched and uniform plant habit.

'Mos Amagren' originated from a hybridization made in January 2006 in a controlled breeding environment in Andijk, Netherlands. The female parent was the unpatented, proprietary plant designated 'CS06-11-2' with larger and fewer leaves, lighter green foliage color and thinner and longer stems.

The male parent of 'Mos Amagren' was the unpatented, proprietary plant designated as 'CS06-14-5' with smaller leaves, less yellow in the leaf color and less serrations. The resultant seed was sown in July 2006.

'Mos Amagren' was selected as one flowering plant within the progeny of the stated cross in September 2006 in a controlled environment in Andijk, Netherlands.

The first act of asexual reproduction of 'Mos Amagren' was accomplished when vegetative cuttings were propagated from the initial selection in September 2006 in a controlled environment in Andijk, Netherlands.

BRIEF SUMMARY OF INVENTION

Horticultural examination of plants grown from cuttings of the plant initiated in September 2006, and continuing thereafter, has demonstrated that the combination of characteristics as herein disclosed for 'Mos Amagren' are firmly fixed and are retained through successive generations of asexual reproduction.

'Mos Amagren' has not been observed under all possible environmental conditions. The phenotype may vary significantly with variations in environment such as temperature, light intensity and day length.

A Plant Breeder's Right for this cultivar was applied for in Canada on Feb. 18, 2010 (#10-6841). 'Mos Amagren' has not been made publicly available more than one year prior to the filing of this application.

The following traits have been repeatedly observed and are determined to be basic characteristics of the new variety. The combination of these characteristics distinguishes this *Solenostemon* as a new and distinct variety.

BRIEF DESCRIPTION OF THE PHOTOGRAPHS

The accompanying photographic drawing shows typical foliage characteristics of 'Mos Amagren' with colors being as true as possible with an illustration of this type. The photographic drawing shows a potted plant of the new variety.

DETAILED BOTANICAL DESCRIPTION

The plant descriptions, measurements and aforementioned photographs were taken in Gilroy, Calif. in early April 2006 in a greenhouse. These plants were about 10-12 weeks old growing in a 4 inch pot.

Color references are made to The Royal Horticultural Society Colour Chart (R.H.S.) 2001.

TABLE 1

DIFFERENCES BETWEEN THE NEW VARIETY 'MOS AMAGREN' AND A SIMILAR VARIETY

| | 'Mos Amagren' | 'Copper' (U.S. Plant Pat. No. 14,394) |
|---|---|---|
| Leaf margin: | Dentate to serrate | Dentate to crenate |
| Leaf shape: | Ovate | Deltoid |
| Petiole length: | 2.3-2.5 cm | 2.5-3.8 cm |
| Petiole diameter: | About 0.3-0.5 cm | 0.25 cm |

Plant:

*Form, growth and habit.*—Annual potted or garden plant grown for its distinctive and colorful foliage; Stems strong, upright and freely branching, moderately vigorous growth habit.

*Plant height.*—35-38 cm.

*Plant width.*—33-40 cm.

*Garden performance and tolerance to weather.*—Very good.

Roots:

*Number of days to initiate roots.*—About 4 days at about 22 degrees C.

*Number of days to produce a rooted cutting.*—6-8 days at 22 degrees C.

*Type.*—Fine, fibrous, free branching.

*Color.*—RHS N155B but whiter.

Foliage:

*Arrangement.*—Opposite, simple.

*Immature, leaf color, upper surface.*—RHS 7C becoming closer to RHS 5C at the apex end; with RHS 144A margins.

*Lower surface.*—Closest to RHS 5C; with RHS 144B margins.

*Mature, leaf color, upper surface.*—RHS 7D becoming closer to RHS 5D towards the apex end and maturing to almost RHS 4D; with (sometimes) medium to light hues of about RHS 59C basally (sometimes more pronounced under the right conditions); RHS 144A margins.

*Lower surface.*—Closest to RHS 5C; with RHS 144A to RHS 144B margins.

*Length.*—8.7-11.5 cm.

*Width.*—4.2-6.5 cm.

*Shape.*—Ovate.

*Base shape.*—Attenuate.

*Apex shape.*—Acuminate.

*Margin.*—Dentate to serrate.

*Texture, upper surface.*—Pubescent; hirsute.

*Lower surface.*—Pubescent; hirsute mainly on the vein.

*Color of veins, upper surface.*—About RHS 59C basally becoming more like RHS 4D.

*Color of veins, lower surface.*—About RHS 59C but lighter becoming more like RHS 4D.

*Petiole color.*—Closest to RHS 4D with some RHS 59C overlay.

*Length.*—2.3-2.5 cm.

*Diameter.*—About 0.3-0.5 cm.

*Texture.*—Pubescent; scattered pilose.

Stem:

*Color of stem.*—Closest to RHS 59C but lighter.

*Length of stem.*—25-33 cm.

*Diameter.*—0.7 cm.

*Length of internodes.*—3.0-7.0 cm.

*Texture.*—Pubescent; pilose at axis.

Inflorescence: Flowering development was not observed on this plant to this date. Therefore also, seed development has not been observed.

Disease/pest resistance: Disease/pest resistance has not been observed on this hybrid.

What is claimed is:

1. A new and distinct variety of *Solenostemon* plant named 'Mos Amagren' substantially as illustrated and described herein.

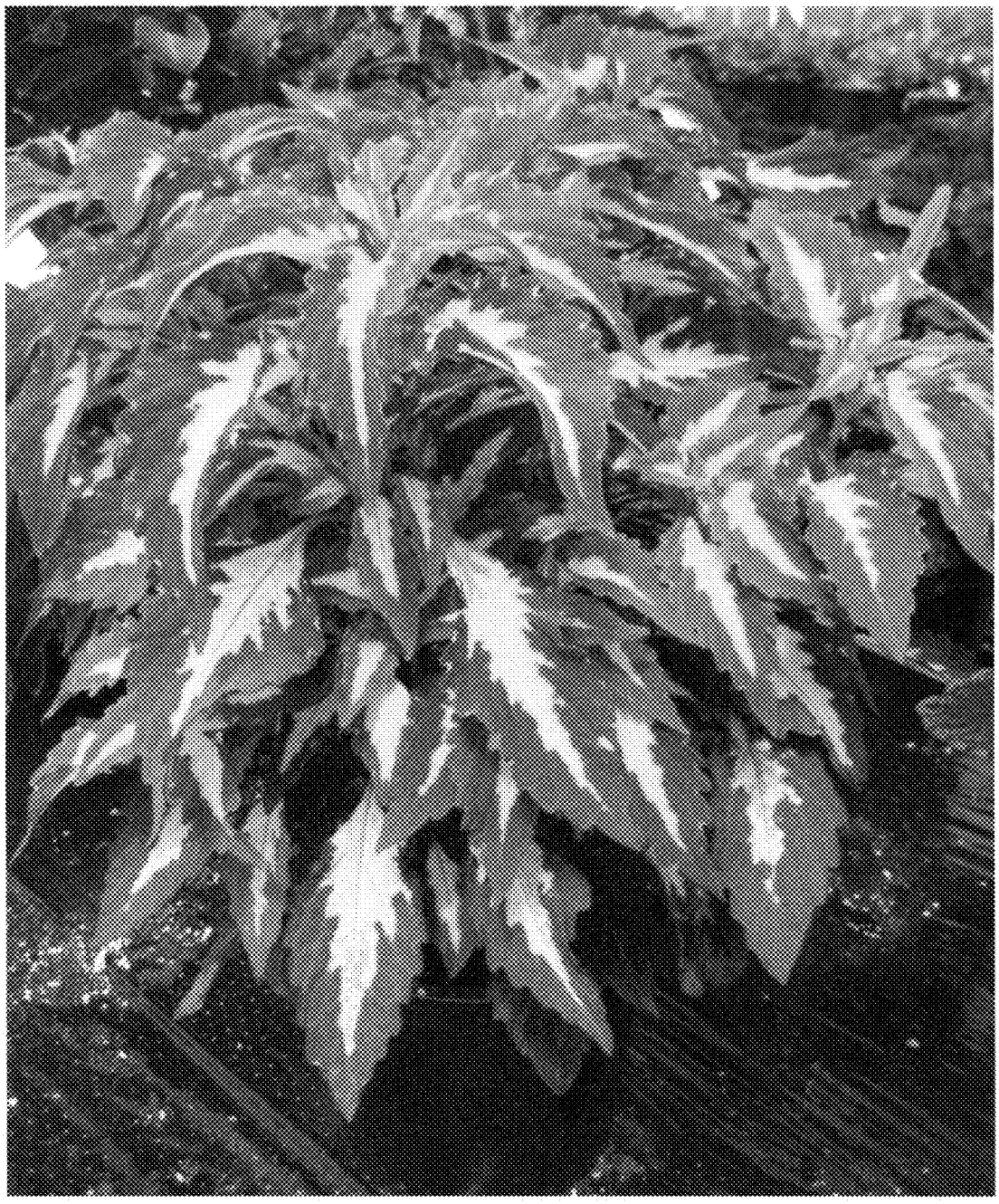

* * * * *